United States Patent
Fishburne, Jr.

(10) Patent No.: US 7,455,521 B2
(45) Date of Patent: Nov. 25, 2008

(54) INTERPROXIMAL DEVICES AND METHODS OF USING SAME

(76) Inventor: Cotesworth Fishburne, Jr., 2611 Carolwood Dr., Rock Hill, SC (US) 29732

(*) Notice: Subject to any disclaimer, the term of this patent is extended or adjusted under 35 U.S.C. 154(b) by 133 days.

(21) Appl. No.: 11/202,740

(22) Filed: Aug. 12, 2005

(65) Prior Publication Data

US 2005/0271999 A1 Dec. 8, 2005

Related U.S. Application Data

(60) Provisional application No. 60/613,449, filed on Sep. 27, 2004.

(51) Int. Cl.
*A61C 3/06* (2006.01)
(52) U.S. Cl. ........................ 433/142; 132/323
(58) Field of Classification Search ............ 433/39, 433/40, 142, 148, 166, 146; 132/323, 328
See application file for complete search history.

(56) References Cited

U.S. PATENT DOCUMENTS

| | | | | |
|---|---|---|---|---|
| 1,201,875 A | * | 10/1916 | Russ | 433/142 |
| 2,288,011 A | * | 6/1942 | Mizzy | 433/148 |
| 2,730,804 A | * | 1/1956 | Saupe | 433/142 |
| 4,304,246 A | * | 12/1981 | Yafai | 132/323 |
| 4,563,152 A | * | 1/1986 | McClure | 433/39 |
| 4,592,729 A | * | 6/1986 | Bilciurescu | 433/142 |
| 4,718,852 A | * | 1/1988 | Galler | 433/148 |
| 4,850,875 A | | 7/1989 | Takatsu | |
| 5,579,786 A | | 12/1996 | Wolk et al. | |
| 6,234,793 B1 | * | 5/2001 | Brattesani et al. | 433/39 |
| 6,386,873 B1 | * | 5/2002 | Blank | 433/142 |
| 6,447,293 B1 | | 9/2002 | Sokol et al. | |
| 2002/0119421 A1 | * | 8/2002 | Gratz | 433/142 |

OTHER PUBLICATIONS

Axis Dental Corp.—Easy in-between—Strips simplify interproximal cleaning, reduction—Dental Products Report—Aug. 2006—p. 54.

* cited by examiner

*Primary Examiner*—Ralph A Lewis
(74) *Attorney, Agent, or Firm*—B. Craig Kilough

(57) ABSTRACT

A loop is formed by a bow having across one side a strip or blade. The bow has flexure and memory. The flexure and memory of the bow are imparted to the strip, enabling the strip to be either taut or loose, depending on the pressure exerted by the operator upon the bow. The bow is held and manipulated by the operator with the thumb and finger. The strip is positioned under tension. A holder for the device allows additional variability in the angle of attack of the strip, and facilitates quick and easy interchange of the strips. A holder avoids insertion of fingers far back in the mouth, where working space is limited.

22 Claims, 8 Drawing Sheets

INTERPROXIMAL DEVICES AND METHODS OF USING SAME

Applicant claims the priority of International Application No. PCT/US04/03785 filed Feb. 11, 2004, which claims priority from Provisional Application Ser. No. 60/447,382 filed Feb. 14, 2003.

Applicant claims the benefit of Provisional Application Ser. No. 60/613,449 filed Sep. 27, 2004.

FIELD OF THE INVENTION

The invention relates to dental devices and methods generally, and is more specifically directed to devices and methods for delivering polishing or cutting strips or points between the contact areas of teeth, resulting in a more convenient and effective methodology to cut, abrade, or polish interproximal surfaces or restorations thereon.

BACKGROUND OF THE INVENTION

It is common knowledge that all surfaces of a dental restoration should be polished. Due to access, the polishing of the interproximal surface of a restoration presents a particular challenge. As used herein, dental "restorations" include, but are not limited to bridges, splints, fillings, caps, veneers, crowns, inlays, and onlays. "Polishing" includes cutting, sawing, and abrading, as well as polishing and flossing. The term "strip" includes a blade as well as a strip or floss. It is common knowledge that interproximal surfaces of teeth may require polishing, regardless of whether restorations are involved, so that the surfaces are cleaner and smoother. It is also common knowledge that a dental restoration should be smoothed (polished), particularly in the gingival area, as rough restorations are a cause of inflammation and other gingival problems. Particularly dangerous to periodontal health are rough ledges or "overhangs" in the gingival areas. Interproximal areas, whether they have restorations or not, should be polished to prevent the accumulation of dental plaque, which is a scummy, bacterial film that can lead to tooth decay, as well as periodontal problems.

There have been recent improvements in polishing modalities for other surfaces of the teeth. However, the standard (conventional) method of polishing the interproximal areas has not changed. With the advent of newer porcelain and composite restorations, the need to polish these interproximal surfaces is more significant.

A standard method of polishing the interproximal areas utilizes narrow (4 mm is typical, although the width may be more or less), five inch (13 cm) strips made of fine sandpaper, diamond-coated metal, linen or other material. As referred to, the "strip" may be made of any of these materials. Limitations in using this (long) strip in polishing methodology include:

Manipulation of the strip requires two (2) hands utilizing four (4) fingers in an area of the mouth having very limited working space. Since two (or both) hands are needed to manipulate the strip, there is no free hand to hold back (retract or protect) the tissues of the mouth, particularly the tongue and the lip(s). The strip as shown in can easily cut these tissues, especially where a heavy lip line is present, and there is no free hand available to hold the lip back. A cotton roll under the lip is sometimes utilized in these situations, but this technique is not always effective in holding the lip back, and commonly, the strip tangles in the cotton fibers. An equally significant factor in the need to hold the lip back is the field of vision—being able to see the objective. Frequently, a cotton roll under the lip further blocks vision.

Because so much of the strip is utilized by the gripping of the fingers, a large percentage of the strip is wasted. This waste is especially significant when employing the costly diamond coated strip, which is in common use.

Control is a problem with a five-inch strip. It is difficult to concentrate the polishing force in a particular area of the surface or the restoration.

While a strip can be pulled forward to polish, it is almost impossible to push to the rear (posterior) of the mouth when one of these surfaces needs to be polished.

While rotary polishing instruments are good for polishing all of the other surfaces of the teeth, the rotary bur, due to the direction it must take in the interproximal areas, can cause uncontrollable and harmful notching of the interproximal surfaces, as in the "flame-shaped diamond" bur.

There is a need for an interproximal polishing device that may be economically produced, may be used while exercising both control and force, may be operated by only two fingers of just one hand, and in which the polishing strip can be held taut for going through the contact area, and taut while being retrieved back through the contact area. There is further need for the same invention which can be angled, and tension selectively and progressively relaxed on the strip for interproximal polishing so as to follow the contour of the tooth with wrap-around capability that does not damage the interdental papilla.

SUMMARY OF THE INVENTION

The present invention is a flexible loop comprising a bow and a strip or blade along a side thereof. The loop is insertable in an interproximal space between adjacent teeth. The bow has flexure and memory in its body and legs. The flexure and memory of the bow are imparted to the strip or blade, enabling the strip or blade to be either taut or loose, depending on the pressure exerted by the operator upon the bow. The loop is held and manipulated by the operator with the thumb and forefinger of one hand. The strip is positioned relative to the bow under tension. A holder for the device allows additional variability in the angle of attack of the strip, and facilitates quick and easy interchange of the strips. The narrow legs of the holder eliminate the insertion of fingers far back in the mouth, where working space is limited. The device of the invention can be used by grasping the bow between a finger and a thumb or by positioning the bow in a holder for the device.

In another aspect, the present invention includes a strip, which may be a blade having a base end and an exposed end. The base end of the strip is pivotally connected to a proximal end of the handle and is adapted to secure the exposed end of the strip upon insertion of the exposed end between predetermined adjacent teeth.

In further aspect, the present invention includes creating or manipulating an interdental space between adjacent teeth by: providing a bow having at least one proximal end and distal end, at least one strip having a base end and an exposed end for insertion in an interproximal space between adjacent teeth, the base end pivotally connected to the proximal end, the distal end adapted to secure the exposed end upon insertion of the exposed end between desired adjacent teeth; inserting exposed end into the desired interproximal space; rotating the bow until the exposed end is secured by distal end; and manipulating the bow to effect the desired interdental spacing.

DESCRIPTION OF PREFERRED EMBODIMENTS

Figure 1:
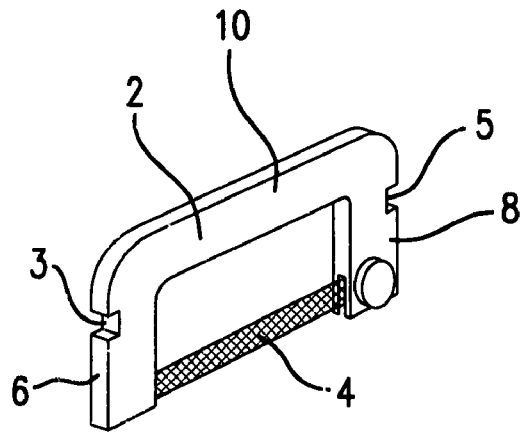
FIG. 1 is a perspective view of an embodiment of the dental apparatus.

In one embodiment, the apparatus of the present invention comprises a manually flexible semi-annular and oblong bow 2. FIG. 1. The bow may be formed of plastic, metal or other materials that are deformable under manual pressure to loosen the strip as described herein, yet have memory to return to the original shape when pressure is released. A strip 4 is mounted/suspended under tension between the ends of the generally vertical legs 6,8 of the bow to form an annular loop. A center member 10 connects the generally vertical legs, and is opposite the strip. As shown, the center member is generally parallel to the strip.

Figure 2:
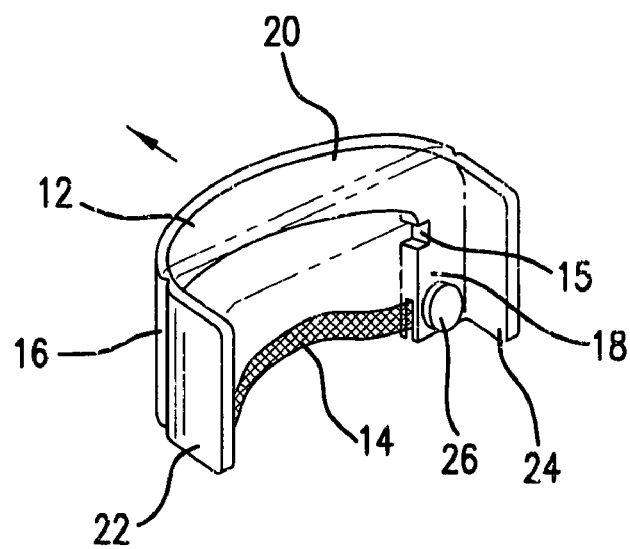
FIG. 2 is a perspective view of another embodiment showing the flexure of the dental apparatus.

In another embodiment, wings for holding and deforming the bow extend from the legs. FIG. 2. A semi-annular bow 12 having a center member 20 connects a generally vertical leg 16 on a proximal end of the bow with a generally vertical leg 18 on a distal end of the bow. The bow has tabs or wings 22,24 extending outwardly from the legs. The bow is capable of deformation by application of manual force applied to the wings, such as by a thumb and forefinger. Upon the application of manual pressure to deform the bow outwardly, so that it is not generally linear, the strip 14 is selectively loosened within the bow to adapt to a non-linear contour of a tooth. Upon release of manual pressure so that the bow is not deformed due to the memory of the bow, the strip becomes taut within said bow. The taut strip facilitates removal of the bow from the interproximal space between adjacent teeth. The strip is capable of insertion into the interproximal space between the adjacent teeth, and the strip is attached to the legs of bow so that the strip is taut when no pressure is applied to the wings.

In the embodiment of FIG. 2, the wings are generally perpendicular to the linear plane of the bow when no pressure is applied. The wings are generally perpendicular to the legs from which they extend. The wings are shown as generally perpendicular to the legs, and are preferred to extend at an angle of 60° to 120° from the legs or the line formed by the bow when no pressure is applied to it. The wings are squeezed between the thumb and a finger of the user, such as a forefinger, to deform the bow and loosen the strip. In the embodiment as shown, the wings extend from substantially the top of the bow to substantially the bottom of the bow.

Figure 3:
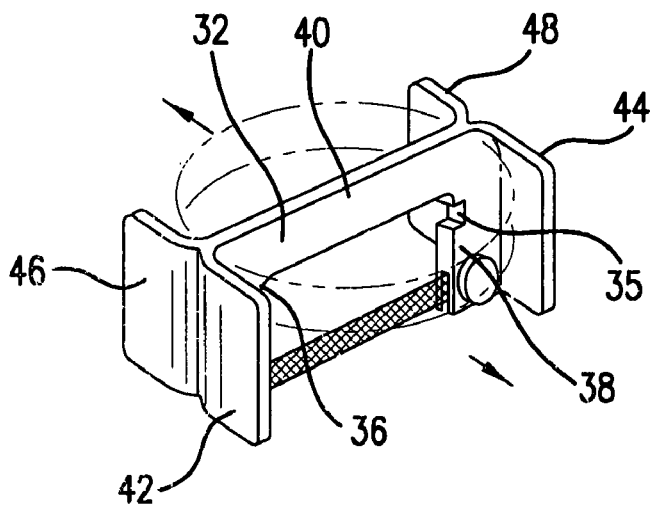
FIG. 3 is a perspective view of yet another embodiment showing the flexure of the dental apparatus.

In another embodiment, wings extend from the legs in each direction. FIG. 3. A semi-annular bow 32 having a center member 40 connects a generally vertical leg 36 on a proximal end of the bow with a generally vertical leg 38 on a distal end of the bow. The bow has tabs or wings 42,44,46,48 extending outwardly from the legs in each direction. The bow is capable of deformation in either direction by application of manual force applied to the wings. Upon the application of manual pressure to deform the bow outwardly, so that it is not generally linear, the strip 14 is selectively loosened within the bow to adapt to a non-linear contour of a tooth. Upon release of manual pressure so that the bow is not deformed due to the memory of the bow, the strip becomes taut within said bow. The taut strip facilitates removal of the bow from the interproximal space between adjacent teeth. The strip is insertable into the interproximal space between the adjacent teeth, and the strip is attached to the legs of bow so that the strip is taut when no pressure is applied to the wings. The wings extending from both sides allow the device to be used on each of the adjacent teeth that border the same interproximal space without removing the device, since the bow can be flexed in either direction according to which pair of wings is squeezed between the thumb and the finger.

The strip may be attached to the bow by a fastener 26, or the strip may be otherwise fixed to the bow. The strip may be inserted as a plastic bow is molded.

The memory inherent in the flexible bow, imparts to the strip a force necessary to keep the strip taut when the bow is released from manual pressure. The flexibility of the bow selectively and progressively loosens the strip as manual pressure is applied to the ends of the bow. In general, the strip is desired to be taut as it pushed down or pulled up between the contacts of the teeth. The strip in one embodiment can be further tightened for positioning the strip between the contacts of the teeth, by the operator pushing the thumb and forefinger towards each other on grips that are provided above the center member. However, most of the tautness of the strip may be built into the bow/strip, by placing the strip under tension between the legs of the bow at the time of manufacture. As shown in FIG. 1 and FIG. 3, the strip is generally linear when taut. The strip is loosened by application of manual pressure to the ends of the bow. FIG. 2.

As used herein, when it is stated that the bow is linear, it means that, when viewed from the top, the bow is formed substantially along a straight line. Similarly, the strip is linear when, when viewed from the top, it is formed substantially along a straight line. In the embodiments of FIGS. 1-3, the strip is aligned with, and is underneath, the bow.

After the strip passes between the contact area of adjacent teeth, the strip can be loosened by positioning the thumb and forefinger towards the ends of the legs of the bow and pushing the opposing legs toward each other to manually deform the bow. The strip loses its linear shape upon manual deformation of the bow, and assumes a shape that is suitable for manipulating the strip against the tooth or other objective having a compound and generally non-linear shape. The operator guides the strip, whenever it is necessary to go under the gum, to the particular side of the interdental papilla in such a manner as to not damage the papilla or the rest of the gum surface. If the surface to be polished is to the front of the papilla, the strip is placed in front of the papilla; and vice-versa for the surface behind the papilla. The bow makes it easy to guide the strip in the placement. The bow may be made of plastic, autoclavable plastic, metal, or other materials having memory that meet the objects of the invention. This invention may embody several different shapes of bows and blades/strips. When used for polishing or cleaning teeth, the strip may be formed of thin, less abrasive material such as linen.

Figure 4:
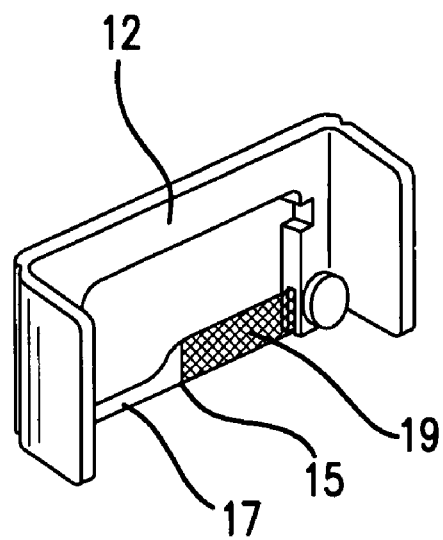
FIG. 4 is a perspective view of still another embodiment of the dental apparatus.

One alternate shape for the strip is shown in FIG. 4. A loop having the structure of the bow of FIG. 2 has a strip with a variable width and multiple surface structures. In particular, the strip 15 of this embodiment may have a smooth surface 17 formed of a material having a low coefficient of friction on one portion, with an abrasive material 19 on another portion of the bow. The area of low friction is used for entering the interproximal area between the teeth. After entry, the bow is flexed by the application of manual pressure as desired, and the abrasive portion of the strip A strip that has an abrasive or is non-abrasive may convey the delivery of anti-caries agents, such as fluorides, or for the delivery of medicaments, such as for the treatment of an interproximal periodontal pocket, or the prevention thereof.

The legs, with the strip attached, may be manually compressed medially as well as pushed towards the posterior (back of the mouth) or pulled towards the anterior (front of the mouth), depending on which surface requires polishing. FIG. 2. This flex allows the body and the legs of the bow to loosen the strip, or force the strip to assume an arcuate shape. It is this loosening of the strip, using manual pressure, and tilting the strip by the thumb and forefinger, that allows the strip to follow the contour of the tooth with a concomitant slight wrap-around effect produced by the arcuate shape. The operator then polishes the area with a sawing (back-and-forth) motion. An up-and-down motion may be used, especially with a narrow strip. In one embodiment, a wing on each of the upper and outer surfaces of the bow are compressed by the operator's thumb and forefinger, causing the legs of the bow to be extended in an outward position, producing additional tension on the strip.

Figure 10:
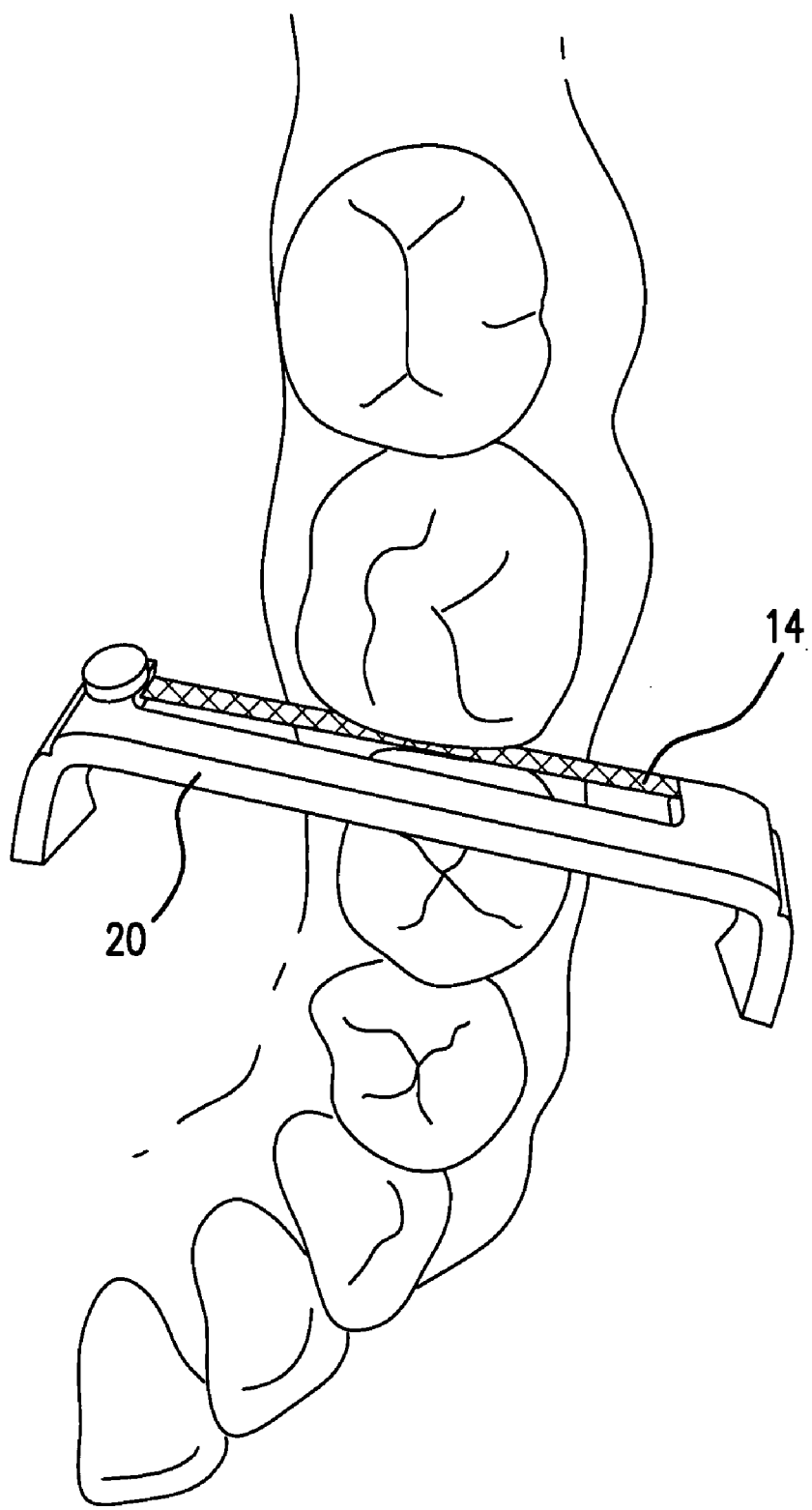
FIGS. 10-12 showing an embodiment of the dental apparatus in use.
Figure 11:
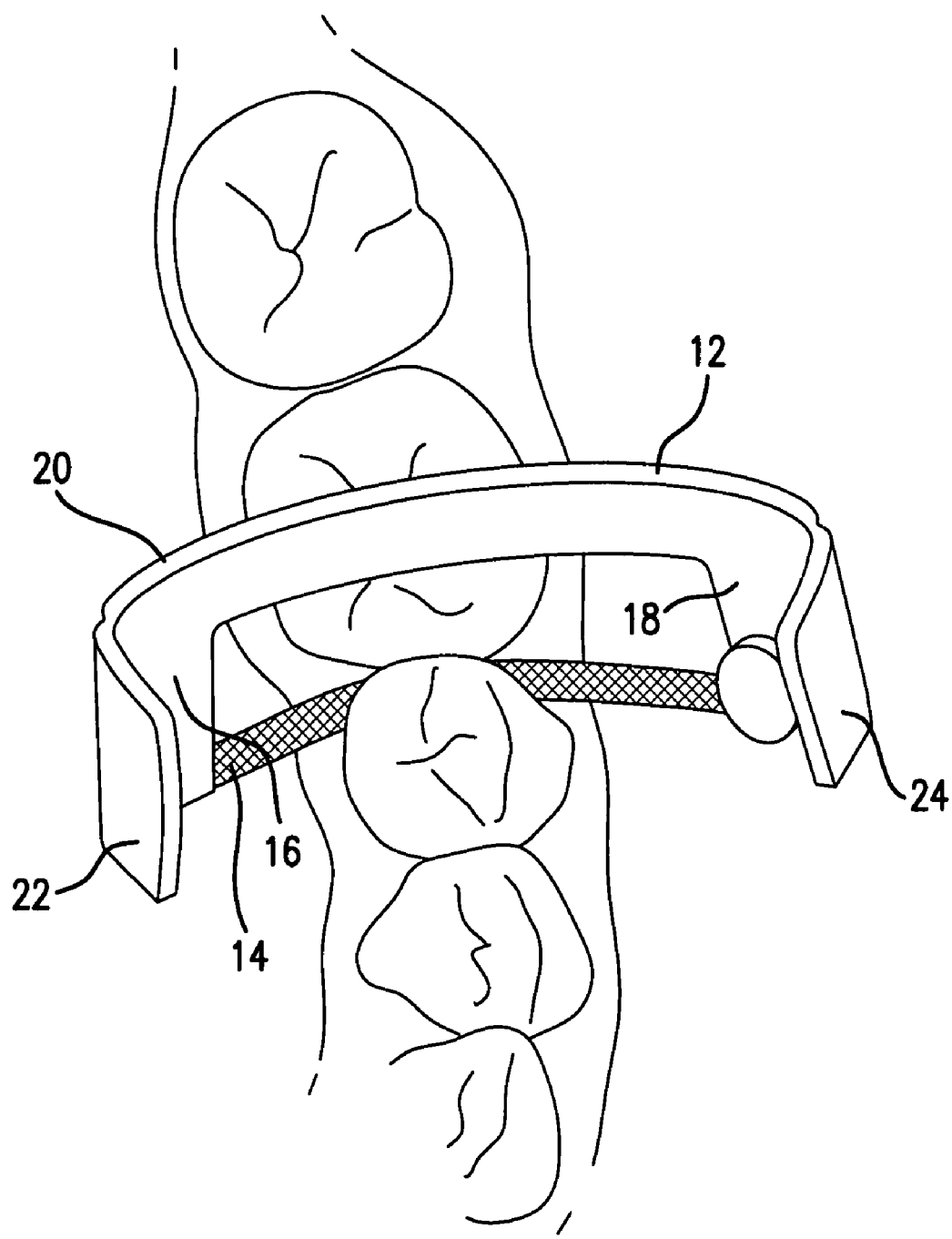
Figure 12:
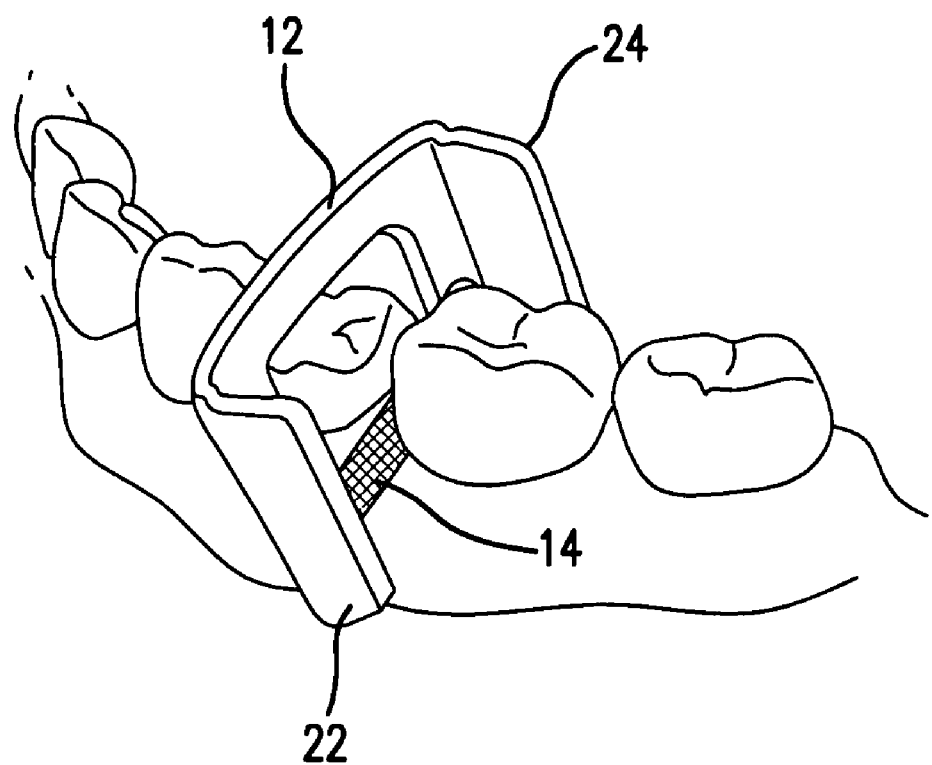

FIGS. 10-12 show a preferred embodiment of the device in use. In FIG. 10, the strip or blade is shown as inserted between the bicuspid and molar in the lower left quadrant of a patient's mouth. In this position, little manual pressure is applied to the ends of the bow, and both the bow and the strip are generally linear, with the strip taut and unflexed. With the strip in the taut and unflexed position, it facilitates penetration of the contact between the bicuspid and molar. When the bow is unflexed, it is in position to smooth an area on the back, tongue side (disto-lingual) of the bicuspid.

FIG. 11 shows the bow being slightly flexed. As the bow flexes, the strip mounting positions are moved closer to each other. Since the mounting positions are relatively closer to each other, the strip is no longer taut, but is loosened, as compared to the strip when the bow is in the position shown in FIG. 10. Since the strip is relatively loose, it may be moved back and forth along the curved surfaces of the tooth. In FIG. 11, the strip is polishing the distal (back) surface of the bicuspid, with the strip contacting the curved, distal surface of the bicuspid.

Additional manual pressure is applied to the ends of the bow, so that it is progressively deformed. If the mounting points of the strip are moved closer together, additional slack is present in the strip. This additional looseness of the strip, while the strip is pulled against the distal surface of the bicuspid, enables a greater surface area on the facial and lingual surfaces of the bicuspid to be polished.

The bow may be tilted slightly from a vertical position. FIG. 12. The upper portion bow is tilted towards the rear (distal) portion of the tooth, which allows the strip to tilt and better engage the surface of the tooth as the bow is pulled forward. The architecture of most teeth is such that they constrict as they join the gum line, and tilting the bow allows the strip to follow the contour of the tooth, providing better engagement of the strip, and the application of additional pressure against the tooth, if desired.

The device may be used in an opposite, so that the device is used to polish the front (mesial) surface of the molar. The bow may be flexed and tilted in an opposite direction.

The device may be used with teeth in the lower front region of the mouth. The operation is being performed with one hand, which allows the operator's opposite hand to, for example, hold the patient's lip away from the bow. With the bow held so that it is generally linear, and the attachment points of the strip relatively far apart, the strip is relatively linear and taut. The memory of the bow assumes the relatively linear shape when no pressure beyond that necessary to hold the bow is applied to the wings or tabs of the bow.

In the embodiments of FIGS. 1-4, when manual pressure is applied to the wings or tabs of the device to move the mounting points of the strip toward each other, slack is introduced to the strip.

The strip may be placed slightly under the gum (gingival papilla) without damage to the gum. Pressure is applied to the bow until the desired level of looseness or slack is achieved in the strip, and the device is tilted as desired to achieve the desired angle of attack for the strip relative to the teeth and gums.

The legs may be formed to be narrow, and the strip is attached to lower wings or tabs. The use of lower wings or tabs facilitates the narrower legs, which facilitates use of the device in the back of the mouth, where working space is particularly critical.

Figure 5:
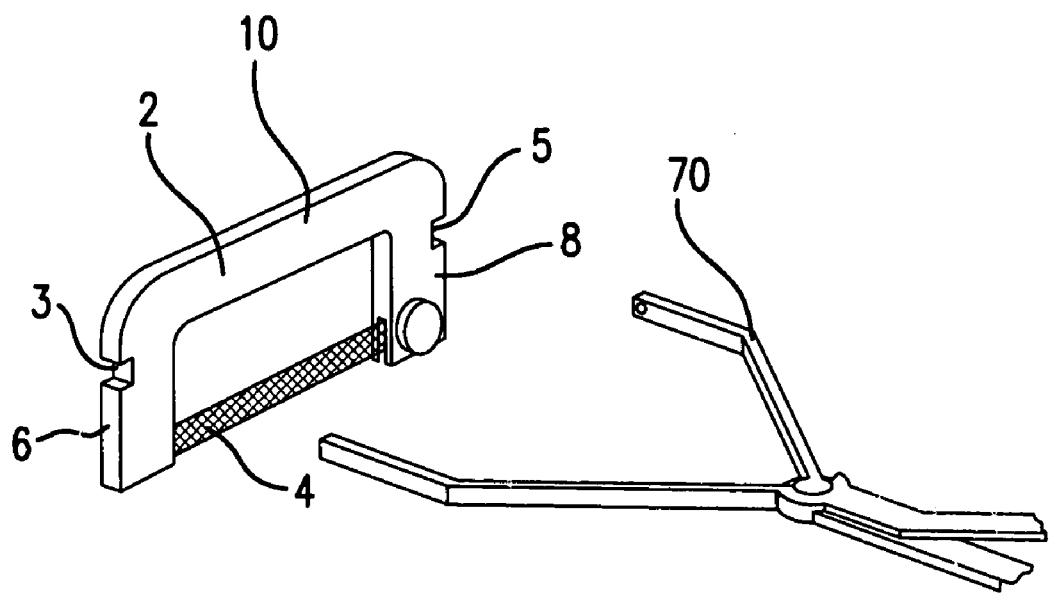
FIG. 5 is a perspective view of the device being used with a holder.

Another embodiment incorporates a bow holder, which facilitates the use of, but is not limited to use with, the bow described above. This invention comprises a metal or plastic two-prong fork 70. FIG. 5. The ends (or legs) of the Y shaped fork can be compressed inwardly with lateral manual pressure.

The ends of the fork can be inserted into the notches 3,5 of the bow of FIG. 5, or notches 15, 17 of the bow of FIGS. 2-3. Through notches or slits in the proximal sides of the bow, as well as the notches or slits in the legs of the fork, the bow is held in place. It is not always necessary to have notches/slits in the legs of the bow, however. The particular grooves, preferably cut at right angles on the inner surfaces of the fork, can hold the bow secure at a right angle to the fork (holder). Other grooves in this same area, preferably cut at 45 degree angles, can hold the bow at the preferred 45 degree angle. The bow can be held at a 45 degree angle facing outward, or the bow can be disconnected, the holder turned upside down (rotated 180 degrees) and the bow can be replaced in the same 45 degree grooves, so that the bow faces inwardly.

As shown in the embodiment of FIG. 5, the Y shaped ends of the fork may be squeezed together to remotely apply pressure to the ends of the bow to deform the bow. The holder may be used to reach into the back of the mouth with the bow holding the strip in the taut position. The strip is inserted in the interproximal space between the teeth. The Y shaped ends of the holder are squeezed together to introduce slack into the strip, and the strip is used as described herein. The memory of the bow returns the holder and the strip to their original position when pressure is released, and the strip may be removed from between the teeth.

In still another embodiment of the holding device, the holder is attached through holes in the bow, with one on each side, and the bow is further stabilized by pushing the forked ends of the major fork through these holes. For the removal, the ends are pinched and removed back through the holes. The holder can be manually operated, or it may be an electromechanical device, such as a reciprocating dental drill or reciprocating powered toothbrush.

In another embodiment, the same principle of the bow is used to hold a metal or plastic matrix band used in the restoring of the interproximal side of a tooth. As with the polishing bow, the matrix band has memory imparted to it from the bow, and the matrix band is taut as it forced between the teeth, and as it is retrieved from between the tooth and a new restoration. Just as with the polishing bow, the bow is flexed at its crest, by the thumb and forefinger, to become more taut when going through the contact area, and is loosened to follow the contour of the tooth, achieve the necessary amount of wrap-around, and provide for a secure contact between the adjacent tooth surface and the new restoration (to prevent food impaction between the adjacent tooth surface and the new interproximal restoration).

The bows and the strips/bands for the matrix system assume several configurations. As the band is flexed, it will "bulge-out" against the adjacent tooth and provide good contact for the upcoming restoration. If desired, an optional cross-wire or a conventional matrix band clip may be placed to hold the legs of the bow in proper position while the restoration is being placed.

Advantages and uses of the bow matrix band technique:

This technique is especially helpful when it is otherwise impossible to get a matrix band completely around the tooth.

With a very deep-seated interproximal cavity preparation, it may be necessary to use a matrix band that is too wide for the traditional retainer but such a band will work in the bow. A deep-seated interproximal cavity is seen frequently after recession or periodontal surgery.

In repairing the gingival seat, the bow is helpful, for example, when it is desirable hold the bow's matrix band tight against the lingual surface while leaving the matrix ban open on the facial surface (the restorative material may be packed from the facial direction.)

Frequently, due to the transparency of the cellophane strip, the strip becomes lost on the bracket table. With a cellophane matrix in a color-coded bow, the operator cannot lose the transparent strip.

The bow matrix retainer of the preferred embodiment is inexpensive to produce and is disposable.

The device may be helpful to achieve good contact between the teeth with composite resin or other dental materials.

The metal, plastic, or autoclavable bow may bend in the direction of the polishing side. This is accomplished by mounting the strip or blade on that side, but may be dictated by tapering the bow at the bottom of its major connector, as well as by hollowing out of this same area on the side toward which the bow is to be flexed. The amount of flexure and directional bending of the legs may be adjusted by similar methods. Tabs or wings 14, 16, at the ends of the legs 6, 8 of the bow 2 determine which way the bow bends, through lever action. The lever action, through these wings, enables the operator to bend the legs with greater facility, allowing the strip to more closely conform to the contour of the tooth, and allowing the operator to control the degree of flexure required.

The angle of the bow's major connector also determines the "rise" of the legs 6, 8 of the bow 2 as well as the way certain areas of the bow are "hollowed-out" to control its direction and amount of bending. A "thin-leg" bow allows more room for the strip. Note that the mouth has plenty of room for a bow in an anterior-posterior (front-to-back) dimension but not, in the posterior part of the mouth, in a lateral dimension.

In one embodiment, the strips are attached to the bow 2 by small protrusions or hooks that are a part of the material of the legs, but which protrude outwardly from the ends of the legs, to allow for the attachment of the strip thereto. This method of attachment allows for replacement of strips.

Other methods of attachment of the strips to the bow are:

Brads, staples, or rivets.

Soldering or stamping the strips into the ends of metal legs.

Heat-melting the strips into the ends of the plastic legs.

Alternatively, the strip area is not attached to the bow, but is formed as an inherent part of the bow. The strip in this embodiment is a very thin, continuous part of the bow. The strip may become a polishing agent by treating it with an abrasive, or by abrading the thin surface.

Among the advantages of the present invention is that the dental bow may be cheaply produced, and may be heat sterilized (autoclaved), or it may be completely disposable. If the bow/strip is autoclaved and a metal strip is used, the bow-mounted strip will probably fare better in the autoclave because the regular un-mounted metal strip, not stretched under tension, tends to curl in the autoclave in such a manner as it makes its reuse difficult.

A further advantage of the present invention is that a strip too narrow to be manipulated by direct finger contact may be successfully utilized in the bow. Some tasks call for a narrow strip, and it is easier to pass a narrow strip through a heavy contact, resulting in less damage (loosening) to the contact area. Some strips may be "hybrids", that is, the same strip can have a narrow portion for placement through tight contacts, and a wider portion for polishing. The narrow portion may be smooth or gritty. A smooth portion of the strip makes it easier for the strip to go through a tight contact. The narrow portion facilitates upward and downward movement on the tooth to detect overhangs or ledges on the side of the tooth. While it is difficult to position a strip between tight contacts, the bow of the present invention facilitates this task, since the bow can provide a better angle of attack, be controlled better, and assist in the application of additional force in penetrating a difficult contact. The bow is better suited for directing the strip to the areas that need polishing than is conventional strip technology.

While most strips have an abrasive side and a safe side, grit or abrasive on both sides of the strip is sometimes desirable, such as in the case of an orthodontic procedure, to make room for orthodontic bands, or to make space to move teeth into. This device of the present invention is useful with such strips. Since the strip is abrasive on each side thereof, the bow may have tabs facing forward and backward, so that the bow and strip may be flexed in either direction to further contour the adjacent teeth while the strip is still in place between them.

Still another advantage of the present invention is that the bows may be color-coded according to the grit level of the strip. Color coding is not desirable with current strip technology, because the color of the strip may be transferred to the new interproximal restoration or tooth surface. The bow of the present invention may by color-coded, without color-coding the strip. Color coding may also be used to indicate the dimensions or composition of the strip.

In one embodiment, an upper anterior bow, is wider and higher (the anterior teeth are longer than the back teeth) than a posterior bow. This embodiment accounts for fact that the upper front (anterior) part of the mouth provides more operating space, since there is no tongue in the way and a lip that can be held out of the way by that "free" hand.

A summary of advantages of preferred embodiments:

The device may be used with one hand.

While the strip is mounted under tension, the crest of the bow can be compressed by the operator's thumb and forefinger further causing the legs of the bow to be extended in an outward position, producing even more tightness in the strip.

The strip can be manipulated between or retrieved through the contacts of the teeth while the strip is in a taut condition When the strip is loosened by manually flexing the strip, the strip follows the contour of the tooth.

Upon flexing the bow, the strip has a desired wrap-around capability relative to the tooth.

The bow is autoclavable or disposable.

The bow may be color-coded for easy identification— according to degree of grit, size, etc.

The bows may be sufficiently small to be easily accessible in the mouth, i.e. can be used while the patient has his/her mouth open in a comfortable position.

Due to its small size and construction, the bow is protective of the soft tissues of the mouth.

The holding device enables the bows to be held securely, yet they can be interchanged quickly.

When used with the holder, the angle of the strip may be changed quickly, to achieve an angle of attack appropriate for the task.

The device can efficiently and effectively polish the mesial surface of the posterior (back teeth) and this cannot be accomplished, except with great difficulty, with previously known devices, since these devices can be pulled forward, but not backward.

The device allows for more control and more force.

The device allows the use of strips that are relatively narrow.

If a metal strip is attached to a bow that can be autoclaved, the (diamond) metal strip will fare much better in the autoclave process than will an unmounted (diamond) metal strip.

The angle of attack of the strip to the tooth may be more easily controlled.

The polishing bow as described will smooth an interproximal rough area. However, a difficult and gross amount of cement, calculus, or rough excess filling material may be present that should be pushed or "chipped out" of the interproximal area. An adjustable "pin ring" positioned on the finger, with a rigid point protruding at a right angle from the surface of the ring, facilitates accomplishment of this task.

After cementing a dental restoration such as a bridge, splint, crown (cap), inlay/onlay or veneer, there often remains a hardened mass of cement that is very difficult to dislodge. Scalers are the accepted method for this removal, but they are time consuming to use, and not sufficiently effective or efficient. Due to the direction of approach to the interproximal space with hand instrument scalers, these scalers are constructed with angles making the scaler susceptible to breaking against hard cement. If an instrument had a direct approach, the chance of fracture of the instrument may be lessened. Traditional thought and design has not allowed this. Also, these traditional hand instruments (scalers) are designed to "pull up", and may dislodge the recently cemented restoration. What is needed is an instrument that is not at a right angle to the mass (as are traditional hand instruments), but which pushes on the mass in a direct fashion. For tactile feel and tactile strength, the new instrument is at the end of the operator's fingertip, not at the far-away end of the handle of the conventional hand instrument. This proximity to the fingertip allows the operator to feel, dislodge, and push the offending mass out of the interproximal space. If the material is allowed to remain, whether it is cement, or a large amount of tenacious calculus, or rough or excess filling material, serious periodontal problems may arise.

An adjustable plastic ring that is positioned over a finger, preferably the first digit of the index finger (the forefinger), and particularly near the tip thereof, is used to remove this material. Protruding from the ring, preferably at a right angle to the ring, is a rigid metal point. If desired, the ring may have a color-coded bottom. While the ring fits comfortably, it is sufficiently firm-fitting to permit it to be angled upwardly or downwardly, front or back, by changing the angle or rotation of the finger. The point may be round, oblong, or triangular, or of other desired shape. This rigid metal point may used for pushing/pulling the device unilaterally through an interproximal space, or it may be opposed by a stipple-surfaced thimble on the opposing thumb of the same hand. The rigid point is pushed by the forefinger through the interproximal space where the point will catch on, or at least be stabilized, in the stippled part to the thumb thimble. Alternatively, a brush, which could be a spiral brush, could be used in place of the pin.

If the rigid point is serrated, abraded, or it is coated with an abrasive substance, a polishing back-and-forth action is accomplished by a sawing action between the thumb and forefinger. The ring of the index finger as well as the ring of the thumb, is easily interchanged to the opposite hand, giving the operator the option of approaching the task from either the lingual or facial side.

Another embodiment of this invention is a thimble for the forefinger that is designed with a hollow tunnel on top (most distal end of the thimble). Into this hollowed tunnel, a blade is inserted. The body of the blade preferred to be is encased in a plastic or rubber sheath that allows the blade to be inserted, with friction, securely into the tunnel. The blade does not rotate or intrude beyond its intended position. The stipple thumb thimble as discussed above may oppose the tip of the blade. The blade may be removed and replaced by another blade of a different shape or grit. Each of the removable blades can be sterilized. The thimble may be worn on either hand for the option of approaching the task from either the lingual or the facial side.

Figure 6:
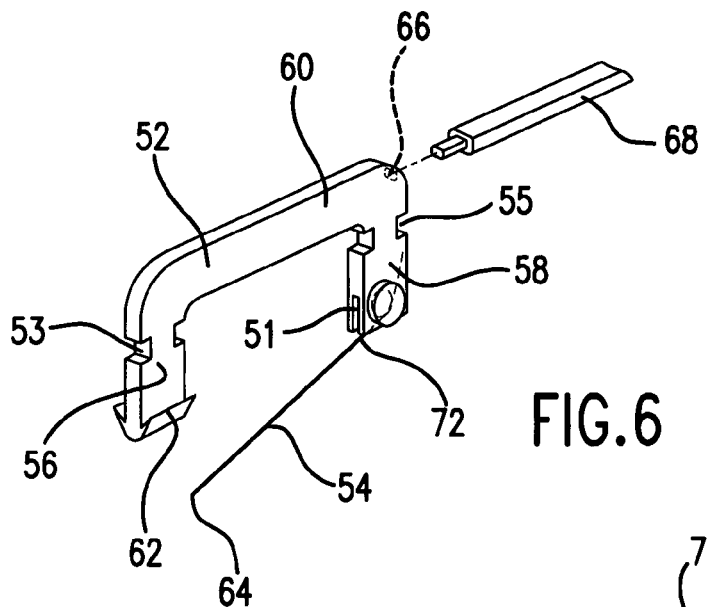
FIG. 6 is a perspective view of a further dental apparatus.

In another embodiment of the device, the strip 54 is attached at one end to a leg 58, or an attached wing, of the bow in a manner that allows the end to pivot. FIG. 6. This end may be mounted with spring biasing. The opposite end fits in a keeper 62 that is present on the opposite leg 56, or an attached wing, of the bow.

Referring to FIG. 6, the apparatus preferably includes a bow 52 having a proximal end and a distal end for securing a strip therein for insertion of an exposed end 64 of the strip in an interproximal space between adjacent teeth. For ease of manipulating bow 52, a recess 66 formed therein adapted to receive at least one of opposed ends of a handle 68. In this construction, the handle aligns with longitudinal axis. Alternatively, the handle shown in FIG. 5 may be used by insertion into notches 53,55.

Bow 52 may have a slot formed in proximal end adapted for securing a base end 72 of the strip therein. A fastener may be provided for the base end, or the base end may be secured within the bow at the time of manufacture. Preferably, a bow permitting ease of angular flexure of the strip is substantially contained within proximal end. The strip extends in a direction away from the base end terminating at tapered exposed end in the embodiment shown. Upon sufficient directed rotation of the strip, which is preferably coplanar with the longitudinal axis, exposed end 64 may be secured in a keeper 62. Once the exposed end is secured in keeper, the strip is structurally supported at its ends. In a preferred use, the exposed end of the strip is directed toward the interproximal space the desired adjacent teeth, which may be by use of a handle connected to the bow as previously discussed, preferably from the facial side toward the lingual side adjacent the sulcus as this typically provides the widest space and therefore the highest chance of insertion of strip there through. To ease insertion, the strip 54 has a flat, narrow profile, but may be triangular shaped to substantially match the shape of the space typically defined by adjacent teeth at the sulcus. After end 64 is sufficiently inserted through the interproximal space, it is desirable to secure the end in the keeper. To effect this securement, the strip is rotated or moved until the end engages the keeper.

Once the end is secured, the bow is manipulated in an effort to further widen/polish or otherwise perform procedures in the interproximal space. Another advantage is acceptance of dental floss there between. This interproximal space widening is accomplished by bringing any combination of upper, lower and lateral surfaces of the strip into abrasive contact with the surfaces between adjacent teeth. To create this abrasive contact, these surfaces may be provided with an abrasive coating, typically comprised of diamond, or by forming discontinuities on these surfaces by exposure to dies under pressure, chemical etching, exposure to high speed particles to cause pitting, or any other method of mechanically changing the surfaces of the strip so that the surfaces are suitable to remove dental material from between adjacent teeth.

Figure 7:
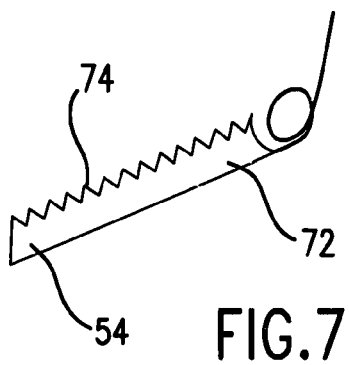
FIG. 7 is a strip for use with the dental apparatus having a serrated blade.
Figure 8:
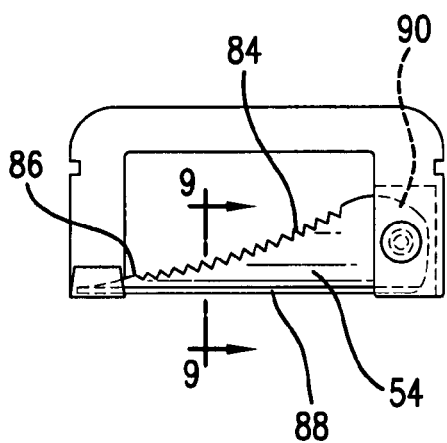
FIG. 8 is an elevation of the loop having a strip or blade for use with the dental apparatus having anther embodiment of a serrated blade.

Referring to FIG. 7, upper surface 74 has formed therein a serrated blade 72. FIG. 8 illustrates an embodiment of strip 54 having a blade 82 formed on upper surface 84 wherein the width of the strip measured from upper surface to lower surface incrementally decreases proceeding in a direction along the length of strip from adjacent bow to end 86, or with the strip in its installed position in the bow, from the proximal end to distal end. Among the advantages of this construction is that in case only a portion of strip may be inserted through interproximal space, the user may nonetheless be able to reciprocate strip to remove composite resin from between the teeth, gradually opening up interproximal space.

Figure 9:
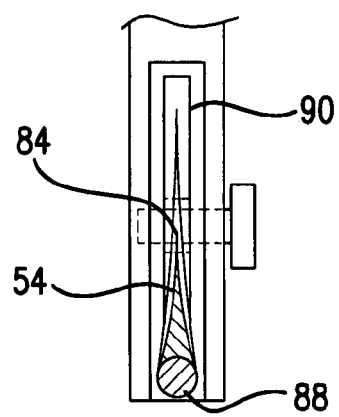
FIG. 9. is a sectioned view of the blade taken essentially along line 9-9 of FIG. 8.

Referring to FIGS. 8-9, although the strip 54 may be of unitary construction, the blade 72,82 may be secured to a wire 88 by crimping, soldering, adhering, use of mechanical fasteners, or any other electrical, chemical or mechanical bonding method that secures the blade to the wire. The strip is provided with a raised portion 90 that when installed in bow 52 is secured within the slot 51 which provides additional lateral support and stability for the strip.

In another embodiment, the blade or strip is a semicircle. Among the advantages of curved blade over a "straight" blade is that a curved blade provides additional usable blade length while utilizing the same attach points of the bow. A blade may be used to separate unwanted contacts, such as when composites bond in an undesired manner.

Once the strip is secured within the bow, the user may apply any combination of horizontal, vertical and torsional forces thereto to remove composite resin material from between adjacent teeth. In each instance, increased surface area contact regions between adjacent teeth result from the application of forces in directions that are substantially perpendicular to the direction of the strip when it is secured in the bow. Although increased surface area contact regions should result in response to any application of forces to bow more preferably, a twisting force most beneficially produces contact regions when applied about an axis that is about forty five degrees or less as measured along from axis which corresponds to the direction adjacent teeth extending from the gum line.

Figure 13:
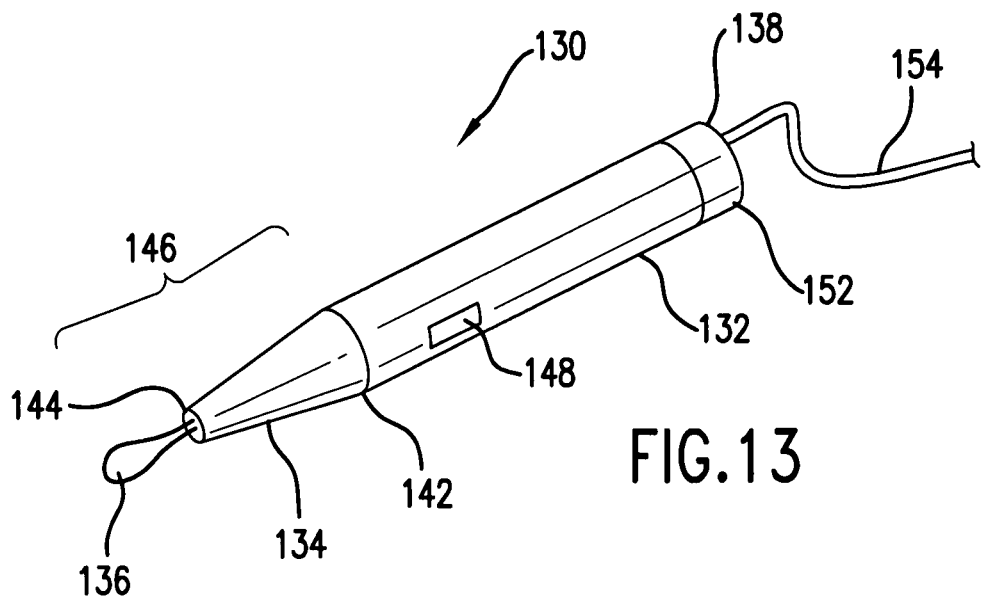
FIG. 13 is a perspective view of an oscillating dental apparatus of the present invention
Figure 14:
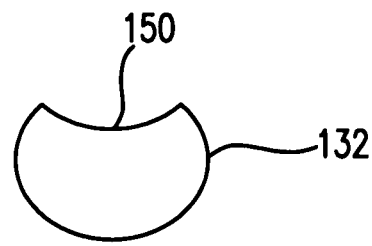
FIG. 14 is a cross sectional view of the oscillating dental apparatus.
Figure 15:
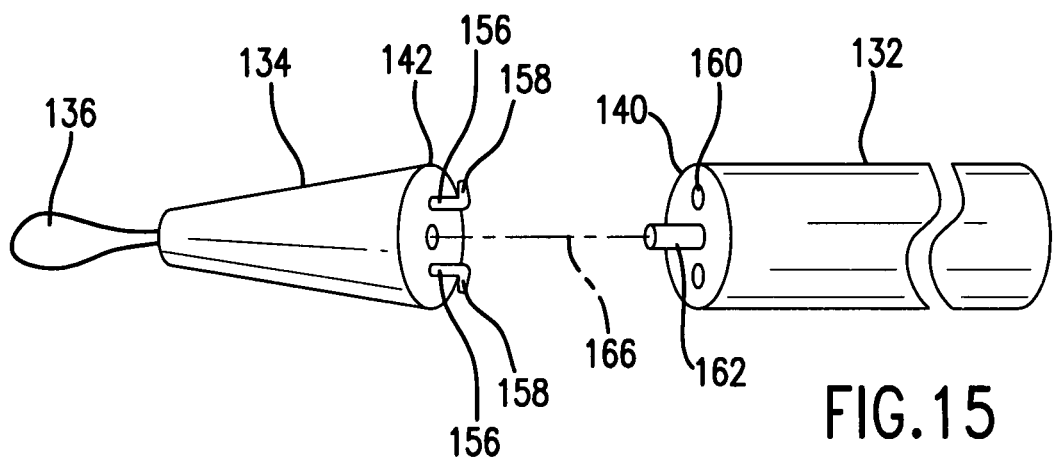
FIG. 15 is an exploded perspective view of the oscillating dental apparatus.

Although not shown, it is readily apparent that the apparatus in FIGS. 1-4, respectively, may be connected to the apparatus of FIGS. 13-15 for providing enhanced insertion and manipulation capability of the strip due to vibrating or reciprocating of the device, including inducing thixotropic behavior in composite resin between adjacent teeth.

An adjustment screw such as at fastener 26 (FIG. 2) may be used to either increase or decrease the amount of tension applied to the strip. However, in the embodiments that are preferred, the strip is taut as manufactured and secured in the bow, and slack in the strip is induced by manual pressure on the ends of the bow that move the ends where the strip is mounted closer to each other.

The flexible strip shown in FIGS. 1-5 and 10-12 may include an abrasive region typically composed of a material having a roughened surface or having abrasive particles (not shown) adhering to the opposing surfaces of portion, including a coarse sandpaper strip to a fine linen strip. The grit size of the abrasive particles may vary widely to accommodate the desired application. In other embodiments, an abrasive region may be interposed between two fibrous regions. The fibrous region may include a central portion which is composed of soft, resilient fibers. The central portion may transition into an outer portion that is composed of tough, less resilient fibers or cloth. The composition of these fibers is limited only by their ability to conform with applicable dental industry regulations as well as having sufficient strength to function as intended. Preferably combined widths W of the strip of FIGS. 1-4 are from about 10 to about 50 percent of the entire length of the strip. Typically, the strip measures from about 1 to 2 inches in length and from about one sixteenth to about one half of an inch wide. The loop may be manually manipulated, or connected to a handle or by a mechanical device (such as described hereinafter) preferably reciprocating at about 3,000 RPM with a thrust of about 2 to about 3 millimeters, although acceptable results may be achieved with a much broader range of reciprocating frequency and thrust length. The bow may have a length of about 2.5-4.5 centimeters and a height of about 1.2-2.6 centimeters.

The operating capabilities of the apparatus may be advantageously enhanced to include a reciprocal motion capability along the tool-holding axis of each apparatus. More preferably, the extent of reciprocal motion is adjustable, such as 15 degrees in each direction, incrementally increasable to up to about 360 degrees, further being capable of controllably adjustable rotational motion along the tool-holding axis, the apparatus even further having the capability to operate with any combination of vibration, rotating or reciprocating motion.

Figure 16:
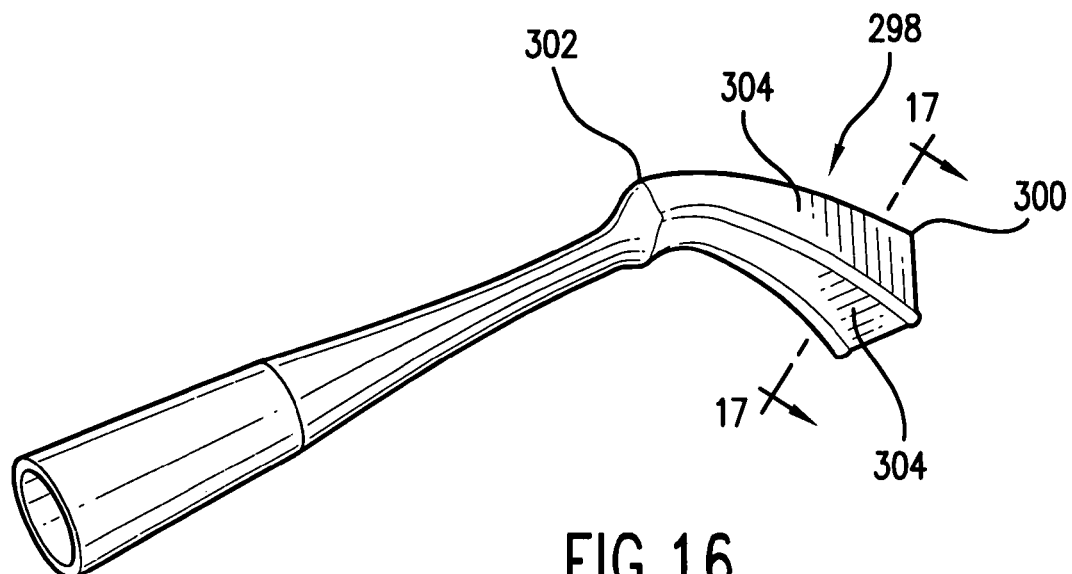
FIG. 16 is a perspective view of a tip for use with the dental apparatus.
Figure 17:
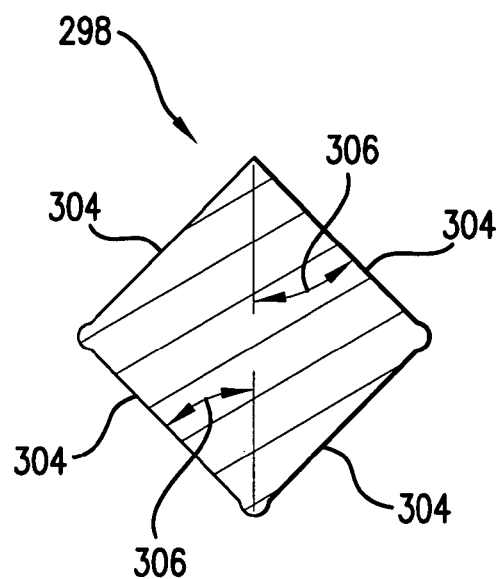
FIG. 17 is a cross sectional view of the tip of FIG. 16.

Referring to FIGS. 16-17, a tip 298 has a novel construction for more precisely locating the composite material between these teeth. Extending from opposed sides of tip 298 are angled surfaces 304 defining preferably symmetric angles 306 along tip 298. Angle 306 which measures in the range of about 30 to about 60 degrees, preferably about 45 degrees, provides an excellent interface with composite resin and the embrasure formed between adjacent teeth. Preferably, the length of angled surfaces 304 along tip 298 incrementally increases, proceeding in a direction from proximal end 302 to distal end 300, as the extent of embrasure typically increases along the mandibular incisors in a direction from the incisal edge to the sulcus. When used with apparatus as previously discussed, tip 298 eases the localized application of composite resin to the embrasures defined between these tooth surfaces by quickly and easily establishing a uniform line of demarcation between the teeth and the dental material. Finally, because dental splints may be applied to either the lingual or labial surface of these teeth, the symmetric construction permits tip 298 to be used on either surface irrespective which tooth surface is used and is compatible for use by both right handed or left handed users without need to obtain another tip.

Referring to the drawings, FIG. 13 illustrates a perspective view of the preferred form of the invention, a dental apparatus 130 for providing preferably low frequency vibration or oscillation that is below the ultrasonic range to a dental restorative material (not shown). As used herein, the term ultrasonic range refers to frequencies in the range of 18 kHz-45 kHz and the term "below the ultrasonic range" below 18 kHz to about 50 Hz. As will discussed in additional detail below, it is also assumed that dental apparatus 130 additionally have the capability to employ in any combination, oscillation, vibration, reciprocation or rotating motion, although it may be that only one motion aspect may be emphasized for use with a particular application. Likewise, the term "oscillating mechanism" may also include the capability for any combination of oscillating, reciprocal or rotating motion. Dental apparatus 130 includes a body 132 having opposed ends 138,140 which preferably secure an oscillation device (not shown) and a power source (not shown) therein. End 140 is securely connected to a proximal end 142 of extension 134 which secures a tip 136 at a distal end 144. The term "tip" may refer collectively to extension 134 and tip 136, such as tip assembly 146, since they may be of unitized construction. Upon actuation of a switch 148, preferably located in an ergonomically favorable location along body 132, vibration device which receives operating power from the power source is urged into operation. Oscillation energy is transmitted along extension 134 to tip 136 for application of oscillation energy to dental preparations as will be discussed more fully below.

Referring to FIGS. 13-14, body 132 is now further discussed. Preferably, body 132 defines an elongated profile for ease of gripping by a user (not shown). Although body 132 is illustrated as a cylinder having a uniform cross section, any cross sectional profile, such as an equilateral or isosceles triangle, or non uniform cross section may be used. In one embodiment, referring to FIG. 14, a hemispherical recess 150 is formed longitudinally along the length of body 132 to enhance user comfort as a resting place for a user's index finger (not shown).

Referring back to FIG. 13, adjacent end 138 of body 132 is cap 152 to secure a power source, such as batteries, therein. Alternately, to supply increased amounts to torque to tip 136 for use with its many possible applications, the power source need not be housed within body 132, and via flexible conduit 154, could deliver operating power to vibrating device from pneumatic, electric, hydraulic or any other mechanical power source, the power source driving the motor housed within body 132 which is compatible with the power source. Securely connected to opposite end 140 of body 132 is tip assembly 146 for transmitting vibratory energy to a dental restoration (not shown). For ease of installation, referring to FIG. 15, extension 134 may be provided with a pair of preferably aligned off-center tabs 156 extending longitudinally from end 142, each transitioning into a radially outwardly extending flange 158 for engaging corresponding apertures 160 formed in end 140 of body 132 when respective ends 140, 142 are placed in mutual axial alignment along axis 66 and directed into contact therewith, to join extension 134 to body 132. To further aid in installation, preferably centered alignment pin 162, which extends longitudinally from end 140 and is slightly longer than the combined length of tab 156 and flange 158, engages centered aperture 164 formed in end 142. It is also preferred that upon adequate insertion of respective flanges 158 inside apertures 160 an audible "click" is produced to indicate proper connection has been established between extension 134 and body 132. Alternately, a mechanical construction may be employed in which upon axially aligned engagement of extension 134 and body 132, extension 134 is directed into a predetermined rotation with respect to body 132 along the mutual longitudinal alignment axis (not shown) to provide a locking feature that is well known in the art.

The oscillating device may be used to apply viscous or thixotropic materials to the surface of teeth. The oscillating device leads to unexpectedly superior results over manual application of these materials. The materials include but are not limited to composite resins and glass ionomer materials.

Prior to the present invention, the material is applied to the surface of the tooth, and manual spread over the surface of the tooth to the desired level. Manual spreading of the material is accomplished by repeatedly tapping the material with a small spatula type device. The material is designed to have substantial surface adhesion so that it will remain on the tooth. The material also has a high viscosity, and is not readily spreadable. In particular, the material tends to stick to the surface of the spatula type spreader, resulting in a certain "pull back" of the material as the spreader is pulled away from the material is successive and repeated taps of the spreader against the material that is present on the surface of the tooth.

The use of the oscillating device will much more quickly spread the material. Unexpectedly, there is no resulting pull back, meaning that spreading may be controlled in a superior manner to manual spreading. Further, a surface results that has superior gloss or shine is achieved. The device and method also achieve stronger interdental contacts.

The oscillating device shown in FIGS. 13-15 having a tip 136 formed as a relatively flat surfaced spatula will achieve the method. A battery powered device manufactured by PANASONIC, Model No. Toothbrush EW129 will satisfactorily achieve the method of spreading the viscous dental material as described herein when the spatula device is attached and the battery powered device is set in the vertical mode. A tapping effect is produced on the material by oscillation of the spatula. Other similar devices may be used. It is preferred that the frequency range of the oscillation is between 50 and 200 cycles, with an amplitude of 0.2 to 2 mm. This frequency is higher than is achieved by manually applying the material. The result is less tendency of the material to stick to the spatula, and superior results are achieved. Also, better flow of the material is increased; prepolymerized carving is improved; stronger interdenal contacts are produced; unfilled resin sealants are possible; less requirement for flowable composites; better adaptation of the material to the cavity walls; less film thickness in cementation of restorations; less interlamina voids and increase in hardness. Other configurations of tips may be used, and such tips may be formed of resilient disposable materials, such as soft plastic caps that connect to the powered device such as by means of a wire and plastic adapter.

PANASONIC, Model No. Toothbrush EW129 may also be used in the vertical mode and attached to the loop to produce a reciprocating motion for manipulation of the strip in the interproximal space between adjacent teeth.

The powered device may be used to remove an installed mechanical dental restoration. The vibrating or oscillating mechanism is configured to vibrate or oscillate at a predetermined frequency that below the ultrasonic range. A removal tool is connected to the oscillating or vibrating mechanism so that the tool oscillates or vibrates when the powered device or mechanism operates and at about the same frequency. The tool is placed in physical contact for a predetermined period of time with a mechanical dental restoration that may be secured at least partially inside a tooth by a dental adhesive. The device induces vibration or oscillation along the length of the dental restoration. The dental adhesive becomes loosened due to the movement imparted by the tool, so that the dental restoration may be more easily removed.

The powered device may be used for mixing dental materials when a tip of the appropriate configuration is attached. Tip 136 is an example of a tip that is appropriate for certain applications. The powered device may be used for the placement of posts and dowels.

The tip 136 may be in the form of a small roller. A wire having a plastic roller formed on the end of the wire is used in combination with the oscillating mechanism to apply the material. The roller that rotates about the wire as the oscillating mechanism imparts vibration or oscillation to the roller.

What is claimed is:

1. A loop that is introduced into an interproximal space between teeth, said loop comprising
   a semi-annular bow having a center member that connects a generally vertical leg on a proximal end of said bow with a generally vertical leg on a distal end of said bow, said bow having a wing extending outwardly from said generally vertical leg on said proximal end of said bow and said bow having a wing extending outwardly from said generally vertical leg on said distal end of said bow; and
   a strip that is insertible into an interproximal space between adjacent teeth, wherein said strip is attached to at least one of said generally vertical leg on said proximal end of said bow and said generally vertical leg on said distal end of said bow, and wherein said strip has a base end and an exposed end for insertion in an interproximal space between adjacent teeth, the base end pivotally connected to the proximal end, the distal end adapted to secure the exposed end upon insertion of the exposed end between predetermined adjacent teeth;
   wherein said bow is flexible and has memory, and wherein said bow is capable of deformation by application of manual force applied to said wing extending outwardly from said generally vertical leg on said proximal end of said bow and said wing extending outwardly from said generally vertical leg on said distal end of said bow, and upon manual deformation of said bow, said strip is selectively loosened within said bow to adapt to a non-linear contour of a tooth, and upon the release of manual deformation of said bow, said strip becomes taut within said bow to facilitate removal of said strip from said interproximal space between adjacent teeth.

2. A loop that is introduced into an interproximal space between teeth, said loop comprising
   a semi-annular bow having a center member that connects a generally vertical leg on a proximal end of said bow with a generally vertical leg on a distal end of said bow, and
   a strip that is insertible into an interproximal space between adjacent teeth, wherein said strip is attached to at least one of said generally vertical leg on said proximal end of said bow and said generally vertical leg on said distal end of said bow;
   wherein said bow is flexible and has memory, and wherein said bow is capable of deformation by application of manual force applied to said bow, and upon manual deformation of said bow, said strip is selectively loosened within said bow to adapt to a non-linear contour of a tooth, and upon the release of manual deformation of said bow, said strip becomes taut within said bow to facilitate removal of said bow from said interproximal space between adjacent teeth
   wherein said center member is bowable, and a center portion of said center member deforms arcuately and bows outwardly and away from a palm of a hand of a user as manual pressure is applied to squeeze and deform said bow, and said generally vertical leg on said proximal end and said generally vertical leg on said distal end of said semi-annular bow are moved in a relative direction that is opposite a direction of movement of said center portion of said center member as manual pressure is applied to squeeze and deform said bow.

3. A loop that is introduced into an interproximal space between as described in claim 2, wherein said strip has a base end and an exposed end for insertion in an interproximal space between adjacent teeth, the base end pivotally connected to the proximal end, the distal end adapted to secure the exposed end upon insertion of the exposed end between predetermined adjacent teeth.

4. A loop that is introduced into an interproximal space between teeth as described in claim 2, said strip further comprising a front surface and a back surface, wherein at least one of said front surface and said back surface has an abrasive coating applied thereon.

5. A loop that is introduced into an interproximal space between teeth as described in claim 2, wherein said strip comprises a surface having discontinuities formed therein.

6. A loop that is introduced into an interproximal space between teeth as described in claim 2, wherein said strip is loosened within said bow as said bow flexes in response to a manual force applied to a wing extending outwardly from said generally vertical leg on said proximal end of said bow and a wing extending outwardly from said generally vertical leg on said distal end of said bow by a thumb and a finger of a user, and wherein the amount of surface area contact between a tooth surface of said strip is increased in relation to the manual force applied to said wing extending outwardly from said generally vertical leg on said proximal end of said bow and said wing extending outwardly from said generally vertical leg on said distal end of said bow by a thumb and a finger of a user.

7. A loop that is introduced into an interproximal space between teeth as described in claim 6, wherein said wing extending outwardly from said generally vertical leg on said proximal end of said bow extends generally perpendicularly from said bow and said wing extending outwardly from said generally vertical leg on said distal end of said bow extends generally perpendicularly from said bow.

8. A loop that is introduced into an interproximal space between teeth as described in claim 2, wherein said strip further comprises an upper side and a lower side, the upper side defining a blade.

9. A loop that is introduced into an interproximal space between teeth as described in claim 2, wherein said blade is serrated.

10. A loop that is introduced into an interproximal space between teeth as described in claim 2, wherein a width of the blade measured from the upper side to the lower side decreases proceeding in a direction along the length of the member from the proximal end to the distal end.

11. A loop that is introduced into an interproximal space between teeth as described in claim 2, wherein a width of strip measured from the upper side to the lower side incrementally decreases proceeding in a direction along the length of the member from the proximal end to the distal end.

12. A loop that is introduced into an interproximal space between teeth as described in claim 2, wherein said strip is attached to said generally vertical leg on a proximal end of said bow, and said generally vertical leg on said distal end of said bow.

13. A loop that is introduced into an interproximal space between teeth as described in claim 2, wherein said strip is attached to said generally vertical leg on a proximal end of said bow, and said generally vertical leg on said distal end of said bow, and said bow and said strip form an annular loop.

14. A loop that is introduced into an interproximal space between teeth as described in claim 2, wherein said strip is attached to said generally vertical leg on a proximal end of said bow, and said generally vertical leg on said distal end of said bow, and said bow and said strip form an annular loop having a central void therein.

15. A loop that is introduced into an interproximal space between teeth as described in claim 2, said strip further comprising a smooth surface having no abrasive material thereon.

16. A loop that is introduced into an interproximal space between teeth as described in claim 2, wherein said strip is a matrix band.

17. A loop that is introduced into an interproximal space between teeth as described in claim 2, further comprising a Y shaped holder having opposing legs, wherein each of said opposing legs engages one of said generally vertical leg on said proximal end of said bow and said generally vertical leg on said distal end of said bow.

18. A loop that is introduced into an interproximal space between teeth as described in claim 2, wherein the loop is of sufficiently small size that the entire loop may be positioned within a mouth.

19. A loop that is introduced into an interproximal space between teeth, said loop comprising:
  a semi-annular bow having a center member that connects a generally vertical leg on a proximal end of said bow with a generally vertical leg on a distal end of said bow, said bow having a wing extending outwardly from said generally vertical leg on said proximal end of said bow and said bow having a wing extending outwardly from said generally vertical leg on said distal end of said bow; and
  a strip that is insertible into an interproximal space between adjacent teeth, wherein said strip is attached to at least one of said generally vertical leg on said proximal end of said bow and said generally vertical leg on said distal end of said bow, and wherein said strip further comprises an upper side and a lower side, the upper side defining a blade, wherein a width of the blade measured from the upper side to the lower side decreases proceeding in a direction along the length of the member from the proximal end to the distal end;
  wherein said bow is flexible and has memory, and wherein said bow is capable of deformation by application of manual force applied to said wing extending outwardly from said generally vertical leg on said proximal end of said bow and said wing extending outwardly from said generally vertical leg on said distal end of said bow, and upon manual deformation of said bow, said strip is selectively loosened within said bow to adapt to a non-linear contour of a tooth, and upon the release of manual deformation of said bow, said strip becomes taut within said bow to facilitate removal of said strip from said interproximal space between adjacent teeth.

20. A loop that is introduced into an interproximal space between teeth, said loop comprising:
  a semi-annular bow having a center member that connects a generally vertical leg on a proximal end of said bow with a generally vertical leg on a distal end of said bow, said bow having a wing extending outwardly from said generally vertical leg on said proximal end of said bow and said bow having a wing extending outwardly from said generally vertical leg on said distal end of said bow; and
  a strip that is insertible into an interproximal space between adjacent teeth, wherein said strip is attached to at least one of said generally vertical leg on said proximal end of said bow and said generally vertical leg on said distal end of said bow, and wherein said strip further comprises an upper side and a lower side, the upper side defining a blade, wherein a width of strip measured from the upper side to the lower side incrementally decreases proceeding in a direction along the length of the member from the proximal end to the distal end;
  wherein said bow is flexible and has memory, and wherein said bow is capable of deformation by application of manual force applied to said wing extending outwardly from said generally vertical leg on said proximal end of said bow and said wing extending outwardly from said generally vertical leg on said distal end of said bow, and upon manual deformation of said bow, said strip is selectively loosened within said bow to adapt to a non-linear contour of a tooth, and upon the release of manual deformation of said bow, said strip becomes taut within said bow to facilitate removal of said strip from said interproximal space between adjacent teeth.

21. A loop that is introduced into an interproximal space between teeth, said loop comprising:
  a semi-annular bow having a center member that connects a generally vertical leg on a proximal end of said bow with a generally vertical leg on a distal end of said bow, said bow having a wing extending outwardly from said generally vertical leg on said proximal end of said bow and said bow having a wing extending outwardly from said generally vertical leg on said distal end of said bow;
  a strip that is insertible into an interproximal space between adjacent teeth, wherein said strip is attached to at least one of said generally vertical leg on said proximal end of said bow and said generally vertical leg on said distal end of said bow; and
  a Y shaped holder having opposing legs, wherein each of said opposing legs engages one of said generally vertical leg on said proximal end of said bow and said generally vertical leg on said distal end of said bow;
  wherein said bow is flexible and has memory, and wherein said bow is capable of deformation by application of manual force applied to said wing extending outwardly from said generally vertical leg on said proximal end of said bow and said wing extending outwardly from said generally vertical leg on said distal end of said bow, and upon manual deformation of said bow, said strip is selectively loosened within said bow to adapt to a non-linear contour of a tooth, and upon the release of manual deformation of said bow, said strip becomes taut within said bow to facilitate removal of said strip from said interproximal space between adjacent teeth.

22. A loop that is introduced into an interproximal space between teeth, said loop comprising:

a semi-annular bow having a center member that connects a generally vertical leg on a proximal end of said bow with a generally vertical leg on a distal end of said bow, said bow having a wing extending outwardly from said generally vertical leg on said proximal end of said bow and said bow having a wing extending outwardly from said generally vertical leg on said distal end of said bow; and a strip that is insertible into an interproximal space between adjacent teeth, wherein said strip is attached to at least one of said generally vertical leg on said proximal end of said bow and said generally vertical leg on said distal end of said bow;

wherein said bow is flexible and has memory, and wherein said bow is capable of deformation by application of manual force applied to said wing extending outwardly from said generally vertical leg on said proximal end of said bow and said wing extending outwardly from said generally vertical leg on said distal end of said bow, and upon manual deformation of said bow, said strip is selectively loosened within said bow to adapt to a non-linear contour of a tooth, and upon the release of manual deformation of said bow, said strip becomes taut within said bow to facilitate removal of said strip from said interproximal space between adjacent teeth, and wherein the loop is of sufficiently small size that the entire loop may be positioned within a human mouth.

* * * * *